United States Patent [19]

Conti et al.

[11] 4,299,718

[45] Nov. 10, 1981

[54] PROCESS FOR PREPARING MIXTURES OF PEROXIDES

[75] Inventors: Dino Conti, Milan; Luigi Minotti, Induno Olona; Egeo Sacrini, Milan, all of Italy

[73] Assignee: Montedison S.p.A., Milan, Italy

[21] Appl. No.: 107,873

[22] Filed: Dec. 28, 1979

[30] Foreign Application Priority Data

Dec. 29, 1978 [IT] Italy ............................... 31403 A/78

[51] Int. Cl.³ .................. C11D 3/39; C11D 3/395; C11D 7/54
[52] U.S. Cl. .......................................... 252/186; 8/111; 252/99; 260/502 R; 568/559; 568/563; 568/566; 568/558
[58] Field of Search .................. 252/186, 99; 8/111; 260/502 R; 568/558, 559, 563, 564, 566, 567

[56] References Cited

U.S. PATENT DOCUMENTS

| | | | |
|---|---|---|---|
| 3,015,631 | 1/1962 | McCloskey | 252/186 |
| 3,557,009 | 1/1971 | McCloskey et al. | 252/186 |
| 3,560,395 | 2/1971 | Westbrook | 252/186 |
| 3,645,908 | 2/1972 | Edl et al. | 252/186 |
| 3,649,546 | 3/1972 | McCloskey et al. | 252/186 |
| 3,649,548 | 3/1972 | McCloskey et al. | 568/559 |
| 3,668,139 | 6/1972 | Daniels et al. | 252/186 |
| 3,692,841 | 9/1972 | McCloskey et al. | 568/559 |
| 3,702,869 | 11/1972 | Leveskis et al. | 568/559 |
| 3,945,940 | 3/1976 | Leveskis | 252/186 |
| 3,957,884 | 5/1926 | Bisset | 252/186 |

OTHER PUBLICATIONS

Harrison et al., Modern Plastics, Jan. 1962, pp. 135–141, 163.

Milas et al., J. Amer. Chem. Soc., vol. 85, Jan. 20, 1963, pp. 222–226.

*Primary Examiner*—Benjamin R. Padgett
*Assistant Examiner*—Irwin Gluck

[57] ABSTRACT

A process for preparing peroxidic mixtures, more particularly mixtures of ketone peroxides useful as polymerization initiators for unsaturated polyester resins, is disclosed. The process comprises in situ peroxidation of one or more ketone compounds with hydrogen peroxide, in a solvent which is a ketone peroxide formulation.

13 Claims, No Drawings

PROCESS FOR PREPARING MIXTURES OF PEROXIDES

THE PRIOR ART

It is known from the literature (Modern Plastics, Jan. 1962, pages 135-163) that some organic peroxides, when used as polymerization initiators for unsaturated polyester resins, interact with each other causing unexpected effects. In fact, numerous catalytic systems comprising two or more peroxides may display a synergic activity, that is, an activity different from the resultant of the activities of the single components of the catalytic system.

Although the catalytic systems having one peroxide generally solve the greatest part of the application requirements for use as polymerization initiators, the catalytic systems having more than one peroxide can solve some particular problems, such as, for instance, long "pot life" of the unsaturated polyester resin additioned with peroxide only, at room temperature, associated with fast gel and hardening times or with long gel times associated with fast hardening times.

For this purpose, in general there are used combinations of normal commercial formulations of individual organic peroxides, added separately to the unsaturated polyester resin at the moment of the use.

Moreover, there is the possibility of using, for the above said purpose, mixtures of preformed peroxides prepared singly and compatible with each other and that will form mixtures that have storage stability and are safe in handling.

There is known, also, from U.S. Pat. No. 3,015,631, the possibility of obtaining mixtures of ketone peroxides that are stable when stored and safe to handle, by carrying out the peroxidation, with hydrogen peroxide, of two or more ketones simultaneously, in the presence or absence of phlegmatizing diluents, by using catalysts such as inorganic or organic acids, cationic resins, or mineral clays.

These methods of mixed syntheses have the limitation in that they can be carried out only with ketones that require a very similar concentration of hydrogen ions for the peroxidation reaction with hydrogen peroxide.

THE PRESENT INVENTION

One object of this invention is to provide a process for preparing mixtures based on ketone peroxides which require a different concentration of hydrogen ions for the peroxidation, and which it would not be able to attain by physically mixing together two or more preformed formulations, also because of the instability of one or more of the components of the desired mixture and the hazards involved in handling it or them.

This and other objects are achieved by the present invention in accordance with which one or more ketone compounds is or are peroxidized in situ with hydrogen peroxide and in a solvent medium which is a ketone peroxide formulation. More specifically, the process of the invention is carried out in practice using between 0.01 mol and 0.7 mol of ketone compound in 100 g of reaction mass and between 0.03 mol and 1.15 mols of hydrogen peroxide in 100 g of reaction mass, at a peroxidation temperature comprised between 0° C. and 50° C., and for a reaction time comprised between 5 minutes and 16 hours, optionally in the presence of a phlegmatizing agent.

The process of the invention is carried out in two stages, first stage being the preparation of the ketone peroxide formulation to be used as dissolving agent, by peroxidizing one or more ketones which require a higher concentration of hydrogen ions.

Once the first peroxidation stage has been completed, the hydrogen ion concentration is reduced, for instance by treatment with an alkali or by mechanically eliminating the solid reaction catalyst. The concentration of hydrogen ions is reduced so as to become suitable for the subsequent peroxidation of the ketones usable in the second stage.

In the second stage there takes place the peroxidation in situ of the other ketones with hydrogen peroxide. In this way, in the final formulation, the ketone may be either partially or totally peroxidized and the hydrogen peroxide may either be present or absent.

Examples of ketones that may be used in the first peroxidation stage include methylethylketone, methylisobutylketone, cyclohexanone, methylcyclohexanone, 3,3,5-trimethylcyclohexanone, etc., and mixtures thereof.

Examples of ketones that may be used in the second stage of the peroxidation include 1,3-diketones (such as acetylacetone), 1,4-diketones (such as acetonylacetone), $\alpha$-$\beta$, or -$\gamma$-hydroxyketones (such as diacetone alcohol), $\alpha$-$\beta$-, or -$\gamma$-alkoxyketones (such as 4-methoxy-4-methylpentan-2-one), etc., and their mixtures.

The hydrogen peroxide used in the process has a concentration comprised between 35-85% by weight, but preferable between 50 and 70%.

The peroxidation reaction of the second stage, besides being conducted by adding the global quantity of hydrogen peroxide in the second stage, may also be carried out by introducing in the first stage of peroxidation, either all or only part of the quantity of hydrogen peroxide required in the second stage. For instance, it is possible to utilize the quantity of unreacted hydrogen peroxide, which is often present is standard formulations based on ketone peroxides (such as methylethylketone peroxide, methylisobutylketone peroxide, cyclohexanone peroxide, etc.), in order to carry out the peroxidation either totally or partially, of suitable quantities of the ketones usable for the second peroxidation stage. Optionally, in that second stage there may be added one or more suitable phlegmatizing agents in order to obtain an active oxygen content suited for ensuring the stability of the product during storage and its safety during handling in use thereof.

A suitable ketone peroxide formulation, obtainable from the first stage, may allow the operator to proceed with the second stage of the peroxidation without any further addition of phlegmatizers.

The quantities of reactants used for carrying out the second peroxidation stage in the process according to this invention are comprised between the following limits:

(1) ketone peroxidic solution, obtained from the first peroxidation stage, representing the solvent medium: from 5 to 95 g in 100 g of reaction mass;

(2) hydrogen peroxide: from 0.03 to 1.5 mols in 100 g of reaction mass;

(3) ketone or ketones to be either totally or partially peroxidized: from 0.01 to 0.7 mol in 100 g of reaction mass;

(4) possible phlegmatizer for diluting the reaction mass: from 0 to 50 g in 100 grams of reaction mass.

Phlegmatizers which are advantageously employed in this invention are for example, phthalic esters, phosphoric esters, glycols, ether glycols, alcohols, etc. The presently preferred phlegmatizers are: triethylphosphate, dimethylphthalate and dipropyleneglycol.

The peroxidation temperature is preferably maintained between 10° and 35° C., while the reaction time is comprised between 5 minutes and 8 hours.

The resulting mixtures so obtained may contain percentages of active oxygen comprised between 3% and 12%, but preferably comprised between 5 and 10%.

The mixtures that may be prepared by operating according to this invention are preferably constituted of formulations based on: methylethylketone peroxide - acetylacetone peroxide, methylisobutylketone peroxide - acetylacetylacetone peroxide, methylethylketone peroxide - diacetone alcohol peroxide, cyclohexanoneperoxide and methylcyclohexanone peroxide-acetylacetone peroxide.

From such mixtures it is possible to prepare an unlimited number of formulations by suitably varying the quantities of the reactants used in the second-stage peroxidation and thus satisfy the requirements of a much wider field of industrial applications than is normally possible.

Said mixtures of two or more ketone peroxides possess a considerable cross-linking activity when used as polymerization initiators for unsaturated polyester resins.

A further advantage is that with the mixtures of this invention, it is possible to achieve a cross-linking action which it is not always possible to equal by adding the components of the mixtures separately to the resin.

This proves that, with the process according to this invention, one actually achieves the formation of ketone peroxides from ketones, in the second peroxidation stage with $H_2O_2$, and the mixtures thus formed consist of ketone peroxides and not of unreacted mixtures of ketones with $H_2O_2$.

The foregoing is supported by the Nuclear Magnetic Resonance (N.M.R.) analysis to which the mixtures prepared in examples 4–10 below were subjected to prove the formation of 3,5-dimethyl-3,5-dihydroxy-1,2-peroxy-cyclopentane (acetylacetone peroxide) in the mixtures.

The chemical shifts found in all the examined mixtures, as well as their attribution, [see the report of Milas Golubovic et al, J.A.C.S. Vol. 85, pages 222–225 (1963)] are shown in the following Table:

| Group | Chemical Shift* ppm | Atoms of H |
|---|---|---|
| ACETYLACETONE (2,4-Pentane-di-one) | | |
| ketonic form $CH_3-C(=O)-CH_2-C(=O)-CH_3$ | $\overline{CH_3}$ 2.07 | 3 |
| | $\overline{CH_2}$ 3.70 | 2 |
| enolic or kelated form $CH_3-C(OH)=CH-C(=O)-CH_3$ | $\overline{CH_3}$ 2.20 | 3 |
| | $\overline{CH}$ 5.66 | 1 |
| ACETYLACETON PEROXIDE (3,5-dimethyl-3,5-dihydroxy-1,2-peroxycyclopentane) (signals present in all the examples from 4 to 10) | | |
| $CH_3, CH_2, OH / HO, O-O, CH_3$ structure | $\overline{CH_3}$ 1.50 | 3 |
| | $\overline{CH_2}$ 2.50 / 2.58 | 2 / 2 |

*As reference compound there was used tetramethylsilane.

The following examples are given to illustrate the invention in more detail, and are not intended to be limiting.

EXAMPLE 1

A mixture consisting of 33.7 g of $H_2O_2$ at 70% parts by weight (p.b.w.) and 5.7 g of $H_2SO_4$ at 2% p.b.w. was additioned under stirring to a mixture consisting of 23.2 g of methylethylketone (butane-2-one) and 26.8 g of dimethylphthalate, over a period of time of about 30 minutes. This reaction mass was cooled externally with water in order to prevent the temperature from exceeding 35° C., and then stirred for a further 2 hours, at 30° C.

The reaction mass was treated with an aqueous solution of NaOH (0.15 N) in such a quantity as to adjust the pH to between 4.0 and 4.5.

The organic phases thus obtained were separated and the organic solution consisting of methylethylketone was washed with a solution saturated with ammonium sulphate and then dried on anhydrous sodium sulphate.

Thereby were obtained 67.7 g of methylethylketone peroxide solution containing 12.3% of active oxygen. To this solution were added 24.8 g of dimethylphthalate and there were obtained 92.5 g of a ketone peroxide formulation based on methylethylketone peroxide (MEKP) in dimethylphthalate containing 9.0% in active oxygen and having a final pH of about 4.5.

This formulation can be conveniently used either as a polymerization initiator for unsaturated polyester resins with a gel time of 14 minutes and a hardening time of 29 minutes, or as a solvent medium for carrying out the peroxidation of further ketones with hydrogen peroxide.

EXAMPLE 2

A mixture consisting of 31.93 g of $H_2O_2$ at 85% p.b.w. and 15.1 g of $H_2SO_4$ at 12% p.b.w. was added, under stirring, to a mixture consisting of 39.84 g of methylisobutylketone (4-methyl-pentane-2-one) and 39.21 g of dimethylphthalate, over a period of time of about 45 minutes. The reaction mass was kept cool from the outside by means of water, in order to prevent the temperature from exceeding 30° C. The organic phase thus obtained was then separated from the aqueous phase and the organic solution containing methylisobutylketone peroxide was treated with an aqueous solution of sodium hydroxide (0.2 N) in such a quantity to attain a pH comprised between 4.0 and 4.5.

The organic solution was then washed with a saturated solution of ammonium sulphate and dried over anhydrous sodium sulphate.

Thereby were obtained 98.3 g of a ketone peroxide formulation based on methylisobutylketone peroxide containing about 10.1% of active oxygen, and having a pH of about 4.5.

This formulation may be conveniently used as a polymerization initiator for unsaturated polyester resins having a gel time of 13.3 minutes and a hardening time of 28 minutes, as well as a solvent medium for carrying out the peroxidation of further ketones with hydrogen peroxide.

EXAMPLE 3

This example reports the composition of a known formulation based on acetylacetone peroxide (AAP) usable as polymerization initiator for unsaturated polyester resins:

| | | |
|---|---|---|
| 3,5-dimethyl-3,5-dihydroxy-1,2-peroxycyclopentane | 33.5% | by wt. |
| water | 6.5% | by wt. |
| triethylphosphate | 60.0% | by wt. |
| active oxygen | 4.06% | by wt. |
| gel time | 13 | min. |
| hardening time | 19 | min. |

This formulation is physically mixed together with the formulation constituted by MEKP, prepared according to Example 1, in order to carry out a comparison between the cross-linking activity of the physical mixtures thus obtained with the cross-linking activity of the mixtures obtained by the two-stage peroxidation according to the present process. The results are reported in Example 11 below.

For this purpose, in the following Example 4, there is reported the preparation of the formulation obtained by physically mixing together MEKP with AAP (acetylacetone peroxide), and in Examples 5 to 10 are described the preparations of the formulations obtained by peroxidation according to this invention.

EXAMPLE 4

Operating at 25° C., with stirring times of 30 min., there were prepared, by physical mixing, formulations A, B, C, D, E and F, having the following compositions:

| | COMPOSITION | |
|---|---|---|
| Formulation | MEKP Formulation in % | AAP Formulation in % |
| A | 53.0 | 47.0 |
| B | 59.3 | 40.7 |
| C | 64.0 | 36.0 |
| D | 77.3 | 22.7 |
| E | 83.8 | 16.2 |
| F | 92.5 | 7.5 |

The MEKP formulation was prepared according to Example 1, while the AAP formulation was prepared according to Example 3.

EXAMPLE 5

To 116.6 g of a MEKP formulation at 90% of active oxygen, prepared as described in Example 1, there were added, under stirring, 37.4 g of acetylacetone, over a time period of about 30 minutes. The reaction mass was cooled externally with water in order to prevent the temperature from exceeding 30° C., and it was then kept under stirring for a further 60 minutes at room temperature.

Thereupon, still under stirring, there were added 33.2 g of an aqueous solution of hydrogen peroxide at 60% p.b.w., over a period of about 45 minutes, maintaining the temperature below 35° C.

The reaction mass was then subjected to stirring for a further 90 minutes at a temperature of 30° C. and finally was additioned with 32.8 g of triethylphosphate so as to obtain 220 g of a mixture based on MEKP and AAP having an active oxygen content of 9%.

EXAMPLE 6

To 154.2 g of a MEKP formulation at 9.0% of active oxygen, prepared as described in Example 1, were added, under stirring, 59.0 g of triethylphosphate, while keeping the reaction mass under stirring for 10 min. at room temperature.

Thereupon, there were added 10.1 g of acetylacetone in 15 minutes, cooling down the reaction mass so as to maintain a temperature not exceeding 30° C.

The reaction mass was then maintained under stirring at room temperature for another 30 minutes, after which it was additioned with 36.7 g of an aqueous solution of $H_2O_2$ at 60% pbw for 35 minutes, maintaining the temperature below 30° C.

The reaction mass was maintained under stirring for another 60 minutes at 30° C., obtaining at the end 260 g of a mixture MEKP/AAP having an active oxygen content of 9.3%.

EXAMPLE 7

To 211.2 g of a MEKP formulation at 9.0% of active oxygen, prepared as described in Example 1, there were added, under stirring, 8.9 g of an aqueous solution of $H_2O_2$ at 60% pbw in 20 minutes, the reaction mass being cooled so that the temperature did not exceed 25° C.

There were then added 21.8 g of triethylphosphate in 15 min. at room temperature, under constant stirring, after which 88.1 g of acetylacetone were added in 60 minutes, keeping the reaction mass under cooling so that the temperature did not exceed 30° C. The reaction mass was then maintained under stirring for a further 90 minutes, thereby obtaining 330 g of a mixture based on MEKP and AAP at 6.5% of active oxygen.

EXAMPLE 8

To 239.6 g of a MEKP formulation at 9.0% of active oxygen, prepared as described in Example 1, there were added, under constant stirring, 28.5 g of $H_2O_2$ at 50% pbw in 30 min., cooling the reaction mass in such a way as to maintain a temperature not exceeding 30° C.

Thereafter were added 14.0 g of acetylacetone in 60 min. maintaining the temperature below 25° C. by means of external cooling. The reaction mass was maintained under stirring for another 120 minutes at 25° C.

Finally, the reaction mass was additioned with 27.9 g of triethylphosphate in 30 minutes at 25° C., thereby obtaining 310 g of product. The MEKP/AAP mixture thus prepared had an active oxygen content of 9.1%.

EXAMPLE 9

To 192.7 g of a MEKP formulation at 9.0% of active oxygen, prepared as described in Example 1, and under stirring and cooling, there were added in 30 min. 11.5 g of $H_2O_2$ at 70% parts by weight. The temperature was maintained at 20° C. Thereafter the mass was additioned with 15.0 g of dimethylphthalate in 10 minutes at room temperature.

Finally, still under stirring, there were added 10.8 g of acetylacetone in 30 minutes, while maintaining the temperature at 35° C.

The reaction mass was kept under stirring for a further 45 min. at 35° C., after which it was cooled down, thereby obtaining 230 g of a MEKP/AAP mixture containing 9.2% of active oxygen.

EXAMPLE 10

To 333 g of a MEKP formulation at 9.0% of active oxygen, prepared according to Example 1, and maintained under stirring at a temperature of 25° C., there were simultaneously added 9.7 g of $H_2O_2$ at 60% p.b.w. and 17.3 g of acetylacetone in 30 min.

The reaction mass was then maintained under stirring at 25° C. for a further 60 minutes. Thereby were obtained 360 g of a MEKP/AAP mixture having an active oxygen content of 8.5%.

EXAMPLE 11

The characterization of the cross-linking activity of the formulations described in Examples 4 to 10 was carried out using an unsaturated polyester resin of the following composition:

| phthalic anhydride | 0.6 mol | |
|---|---|---|
| maleic anhydride | 0.4 mol | 65% by weight |
| propylene glycol | 1.0 mol | |
| styrene monomer | | 35% by weight |
| hydroquinone | | 130 p.p.m. |
| cobalt octoate (as $Co^{2+}$) | | 90 p.p.m. |

The determinations were carried out in a bath stabilized at 20° C., on 50 g of activated resin with 2% b.w. of each ketone peroxide formulation.

The results of the cross-linking activity, expressed as gel and hardening times, obtained with the formulations described in Examples 4 and 5-10, are recorded in the following tables.

TABLE A

| Formulation Ex. 4 | Gel Time Minutes | Hardening Time Minutes |
|---|---|---|
| A | 15.6 | 23.6 |
| B | 15.9 | 24.3 |
| C | 15.7 | 24.8 |
| D | 15.1 | 26.3 |
| E | 14.8 | 27.0 |
| F | 14.4 | 28.1 |

TABLE B

| Ex. No. | % Formulation MEKP | Gel Time Min. | Hardening Time Minutes |
|---|---|---|---|
| 5 | 53.0 | 12.3 | 19.5 |
| 6 | 59.3 | 10.1 | 19.0 |
| 7 | 64.0 | 15.0 | 23.4 |
| 8 | 77.3 | 12.6 | 22.4 |
| 9 | 83.8 | 13.6 | 24.2 |
| 10 | 92.5 | 24.0 | 37.0 |

These results have been obtained for formulations having a content in MEKP (at 9% of active oxygen) comprised between 53% and 92.5%.

As evidenced by Table A the gel time for the formulations of Example 4 were comprised between 14.4 and 15.9 minutes, while the hardening times were comprised between 23.6 and 28.1 minutes.

In contrast, the gel time for the formulations of Examples 5-10 is comprised between 10.1 and 24 minutes, while the hardening time is comprised between 19 and 37 minutes. As is apparent, it is possible, by the practice of this invention, to achieve wider ranges of gel and hardening times inasmuch as the process allows to vary continuously the quantity of reactants participating in the second peroxidizing stage so that a practically unlimited number of formulations even having an equal content in MEKP is obtained, and thus the possibilities of industrial application are considerably expanded.

The foregoing statement is supported by the following Table C reporting the results of the cross-linking activity, expressed in gel and hardening times, of three formulations in which have been varied the quantities of acetylacetone and maintained constant the quantities of methylethylketone peroxide and hydrogen peroxide in order to obtain formulations having the same content in active oxygen.

TABLE C

| Peroxidic Formulation | | Cross-linking Activity | |
|---|---|---|---|
| Test | MEKP % | Gel time Minutes | Hardening time Minutes |
| a | 75 | 18.7 | 29.3 |
| b | 75 | 13.7 | 26.7 |
| c | 75 | 16.0 | 29.5 |

Test a

To 150 g of a MEKP formulation at 9.0% in active oxygen, prepared as described in Example 1, there were added, under constant stirring, 10.4 g of $H_2O_2$ at 60% pbw in 30 minutes, cooling the reaction mass from the outside so that the temperature did not exceed 30° C.

Thereupon, there were added 16.8 g of acetylacetone in 60 minutes, maintaining the temperature below 25° C., by means of external cooling. The reaction mass was then kept under stirring for another 120 minutes at 25° C.

Finally, in a period of 30 minutes, there were added 22.8 g of triethylphosphate at 25° C. Thereby were obtained 200 g of a MKEP/AAP mixture having an active oxygen content of 8.2%.

TEST b

To 150 g of a MEKP formulation at 9.0% in active oxygen, prepared as described in Example 1, there were added, under stirring, 10.4 g of $H_2O_2$ at 60% pbw in 30 minutes, cooling the reaction mass from the outside so that the temperature did not exceed 30° C.

Thereupon, to that reaction mass were added 4.2 g of acetylacetone in a period of 60 minutes, maintaining the temperature below 25° C. by means of external cooling. This reaction mass was then maintained under stirring for a further 120 minutes at 25° C.

At last, there were added, in a period of 30 minutes, 35.4 g of triethylphosphate at 25° C. Thereby were obtained 200 g of a MEKP/AAP mixture containing 8.2% of active oxygen.

TEST c

To 150 g of a MEKP formulation at 9.0% in active oxygen, prepared as described in Example 1, there were added, under constant stirring, 10.4 g of $H_2O_2$ at 60% pbw, in 30 minutes while cooling the reaction mass from the outside so that the temperature did not exceed 30° C. Thereupon there were added 8.4 g of acetylacetone in 60 minutes, maintaining the temperature below 25° C. by means of outside cooling. The reaction mass was then subjected to stirring for another 120 minutes at 25° C. Finally, there were added to it 31 g of triethylphosphate in 30 minutes at 25° C. There were thus obtained 200 g of a MEKP/AAP mixture containing 8.2% of active oxygen.

EXAMPLE 12

The cross-linking activity of the unsaturated polyester resin of Example 11 was determined by introducing separately in the resin at the moment of the polymerization, the reactants in the ratios used for the preparation of the mixture of Example 7.

The data obtained showed that with the peroxidation method according to this invention the peroxidation of the ketone in the second stage does occur.

TABLE

| | Formulation Used | Concentration on the Resin in % | Gel Time Min. | Hardening Time Min. |
|---|---|---|---|---|
| 1. | Mixture of Ex. 7 | 2. | 15.0 | 23.4 |
| 2. | MEKP Ex. 1 | 1.280 | | |
| | H$_2$O$_2$ 60% | 0.054 | | |
| | Acetylacetone | 0.534 | 8.5 | 16.5 |
| | Triethylphosphate | 0.132 | | |
| | Total: | 2.000 | | |

EXAMPLE 13

This example demonstrates a peroxidation in which, as a solvent medium, there was used a methylisobutylketone peroxide (MIBKP) formulation at 10.0% in active oxygen, in order to carry out the peroxidation of acetylacetone with hydrogen peroxide.

To 160 g of a MIBKP formulation containing about 10.0% in active oxygen, prepared as described in Example 2, there were added, under constant stirring and by maintaining the temperature below 30° C. by external cooling, 20 g of acetylacetone over a period of 30 minutes.

The reaction mass was then maintained under constant stirring for another 30 minutes, after which, in 45 minutes, there were added 8.8 g of H$_2$O$_2$ at 60 pbw, maintaining the temperture below 35° C. The reaction mass was then subjected to stirring for a further 45 minutes after which 28.6 g of triethylphosphate were added so as to obtain a mixture based on MIBKP and AAP containing 8.5% of active oxygen.

The cross-linking activity of the unsaturated polyester resin of Example 11 was then determined with the following results: gel time=15.8 minutes; hardening time=24.8 minutes. The concentration of the MIBKP/AAP mixture in the resin amounted to 2%.

EXAMPLE 14

An example of peroxidation of diacetone alcohol with hydrogen peroxide was carried out using a MEKP formulation as solvent medium.

To 320 g of a MEKP formulation at 9.0% of active oxygen, prepared as described in Example 1, there were added, under stirring and maintaining the temperature below 25° C., and in a period of 20 minutes, 40 g of diacetone alcohol (4-methyl-4-hydroxy-pentane-2-one).

The reaction mass was subjected to further stirring for another 40 minutes at 25° C. and then, in a period of 30 minutes, there were added 17.6 g of H$_2$O$_2$ at 60 pbw., maintaining the temperature below 30° C. Stirring was resumed for another 60 minutes at 30° C., after which 22.4 g of triethylphosphate were added.

There were obtained 400 g of a mixture based on MEKP/diacetone alcohol peroxide with a content in active oxygen of 8.5%.

The data on the cross-linking activity with the unsaturated polyester resin of Example 11 was as follows: gel time=10.4 minutes; hardening time=23.4 minutes. The concentration of mixture MEKP/DAAP in the resin was equal to 2%.

EXAMPLE 15

Acetylacetone was peroxidized with hydrogen peroxide, using as a solvent medium a commercial mixture of cyclohexanone peroxide and methylcyclohexanone peroxide, as follows:

To 200 g of a commercial mixture of cyclohexanone peroxide and methylcyclohexanone peroxide there were added, in a period of 30 minutes, under stirring and maintaining the temperature below 25° C., 50 g of acetylacetone (2,4-pentanedione).

The reaction mass was subjected to further stirring for another 40 minutes at 25° C. and then in a period of 60 minutes there were added 57 g of H$_2$O$_2$ at 60% p.b.w. maintaining the temperature below 30° C. Stirring was resumed for another 60 minutes at 30° C.

There were obtained 306 g of a mixture based on cyclohexanone peroxide, methylcyclohexanone peroxide and acetylacetone peroxide with a content in active oxygen of 8.5%

The data on the cross-linking activity with the unsaturated polyester resin of Example 11 read as follows: gel time=11.6 m; hardening time=23.9 min. The concentration of the mixture of cyclohexanone peroxide and methylcyclohexanone peroxide/acetylacetone peroxide in the resin was equal to 2%.

The ketone peroxide formulation used as a solvent medium in the present process can be prepared by known methods.

We claim:

1. Process for the preparation of mixtures constituted by ketone peroxides, characterized in that a ketone peroxide formulation is used as a solvent medium for the in situ peroxidation of one or more ketone compounds with hydrogen peroxide, using a quantity of ketone compound of 0.01 mol to 0.7 mol in 100 g of reaction mass, and a quantity of hydrogen peroxide of 0.03 mol to 1.5 mols in 100 g of reaction mass, at a peroxidation temperature of 0° C. to 50° C. and for a reaction time comprised between 5 minutes and 16 hours.

2. The process of claim 1, in which the peroxidation is carried out in the presence of a phlegmatizing agent.

3. The process of claim 1, further characterized in that the quantity of ketone peroxide formulation used as the solvent medium is from 5 to 95 g in 100 g of reaction mass.

4. The process of claim 1, further characterized in that the ketones used in preparing the ketone peroxide formulation used as the solvent medium are selected from the group consisting of methylethylketone, methylisobutylketone, cyclohexanone, methylcyclohexanone, 3,3,5-trimethylcyclohexanone, and mixtures thereof.

5. The process of claim 1, further characterized in that the ketone compounds peroxidized in situ, are selected from the group consisting of 1,3-diketones, 1,4- diketones α-β- or -γ-hydroxyketones, α-β- or -γ-alkoxyketones, and mixtures thereof.

6. The process of claim 4 in which the ketone compounds peroxidized are selected from the group consisting of acetylacetone, acetonylacetone, diacetone alcohol, and 4-methoxy-4-methyl-pentane-2-one, and mixtures thereof.

7. The process of claim 1, in which the concentration of the hydrogen peroxide is from 35% to 85% by weight.

8. The process of claim 6, in which the concentration of the hydrogen peroxide is from 50% to 70% by weight.

9. The process of claim 1, in which the peroxidation is carried out at a temperature of from 10° C. to 35° C., and the reaction time is from 5 minutes to 8 hours.

10. The process of claim 2, further characterized in that the phlegmatizing agent is selected from the group consisting of triethylphosphate, dimethylphthalate and dipropylene glycol in a quantity of from 0.5 g to 50 g in 100 g of reaction mass.

11. Mixtures prepared according to claims 1, 2, 3, 4, 5, 6 or 7, and characterized in that they contain formulations based on methylethylketone peroxide-acetylacetone peroxide, methylisobutylketone peroxide-acetylacetone peroxide, methylethylketone peroxide-diacetonealcohol peroxide, cyclohexanonperoxide or methylcyclohexanonperoxide-acetylacetonperoxide.

12. Mixtures prepared according to claim 1, characterized in containing from 5% to 10% parts by weight of active oxygen.

13. The mixtures of claim 1 used as polymerization initiators for unsaturated polyester resins.

* * * * *